United States Patent
Syage et al.

(10) Patent No.: US 9,726,655 B2
(45) Date of Patent: Aug. 8, 2017

(54) SELECTIVE ION CHEMISTRY FOR NITRATE DETECTION

(71) Applicant: Morpho Detection, LLC, Newark, CA (US)

(72) Inventors: Jack A. Syage, Corona del Mar, CA (US); Andrey N. Vilkov, Aliso Viejo, CA (US); Sheng-Suan Cai, Corona, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 255 days.

(21) Appl. No.: 14/492,196

(22) Filed: Sep. 22, 2014

(65) Prior Publication Data

US 2016/0282321 A1   Sep. 29, 2016

(51) Int. Cl.
| | |
|---|---|
| *G01N 31/22* | (2006.01) |
| *G01N 33/22* | (2006.01) |
| *H01J 49/00* | (2006.01) |
| *H01J 49/10* | (2006.01) |
| *G01N 33/00* | (2006.01) |
| *H01J 49/04* | (2006.01) |

(52) U.S. Cl.
CPC ......... *G01N 33/227* (2013.01); *G01N 31/227* (2013.01); *G01N 33/0057* (2013.01); *H01J 49/0027* (2013.01); *H01J 49/10* (2013.01); *H01J 49/04* (2013.01)

(58) Field of Classification Search
CPC ........... G01N 33/0037; G01N 33/0057; G01N 33/22; G01N 33/227; G01N 31/227; Y10T 436/17; Y10T 436/173076; Y10T 436/201666; Y10T 436/24; H01J 49/26

USPC .................. 436/106, 110, 129, 173
See application file for complete search history.

(56) References Cited

U.S. PATENT DOCUMENTS

| | | | |
|---|---|---|---|
| 6,495,824 B1 | 12/2002 | Atkinson | |
| 6,861,262 B2 | 3/2005 | Novinski et al. | |
| 7,015,464 B2 | 3/2006 | Nagano et al. | |
| 7,468,672 B2 | 12/2008 | Harden et al. | |
| 2010/0282962 A1 | 11/2010 | Machuron-Mandard et al. | |
| 2013/0260478 A1 | 10/2013 | Ewing et al. | |
| 2015/0004710 A1* | 1/2015 | Gregory | G01N 33/227 436/75 |

FOREIGN PATENT DOCUMENTS

| | | |
|---|---|---|
| EP | 0655769 A1 | 5/1995 |
| WO | 2014058508 A2 | 4/2014 |

OTHER PUBLICATIONS

Tam et al. Analytical Chemistry, vol. 76, 2004, pp. 2741-2747.*
Cotte-Rodriguez et al., "Desorption Electrospray Ionization of Explosives on Surfaces: Sensivity and Selectivity Enhancement by Reactive Desorption Electrospray Ionization," Analytical Chemistry, 2005, vol. 77, pp. 6755-6764.
Gapeev et al., "Liquid chromatography/mass spectrometric analysis of explosives: RDX adduct ions," Rapid Communications in Mass Spectrometry, 2003, vol. 17, pp. 943-948.

* cited by examiner

*Primary Examiner* — Maureen Wallenhorst
(74) *Attorney, Agent, or Firm* — Armstrong Teasdale LLP

(57) ABSTRACT

The present disclosure is directed to methods and systems for detecting a chemical substance. The methods and systems include mixing a sample of a substance of interest with an additive and then producing an adduct using an ionization source. The systems and methods further include performing a spectrometric analysis of the adduct and identifying the sample using comparative spectrometric data.

20 Claims, 14 Drawing Sheets

SELECTIVE ION CHEMISTRY FOR NITRATE DETECTION

BACKGROUND OF THE DISCLOSURE

The embodiments described herein relate generally to a detection technique for chemical substances, and, more particularly, to using additives to detect contraband substances such as explosives, narcotics, pesticides, and chemical warfare agents by means of spectrometry.

Certain contraband substances—such as ammonium nitrate (AN), ammonium nitrate fuel oil (ANFO) and urea nitrate (UN)—can be difficult to detect through discharge type sources such as, for example, atmospheric pressure chemical ionization (APCI) because the discharge of air generates abundant atmospheric $NO_3^-$ ions that can overlap with the nitrate $NO_3^-$ ion signal from ANFO and UN (as well as other explosives). Known techniques have tried to differentiate the two signal contributions, but the sensitivity is compromised by the background atmospheric $NO_3^-$ signal. Other techniques that are known attempt to bind additives to explosives for detecting chemical substances; however, these techniques are unable to differentiate between $NO_3^-$ ions from the air and nitrate $NO_3^-$ ions from explosives.

In many known substance detection techniques, adduct ions are commonly used. Adducts are products of combining two or more distinct molecules to form a single reaction product containing all of the atoms of all of the component molecules, thereby forming a distinct molecular species. Such distinct molecules may be positive or negative ions and the associated adduct ions are formed in either a positive ion mode or a negative ion mode, respectively, to enhance the sensitivity of spectrometry devices for certain classes of compounds of interest. The use of adducts facilitates ionization through ion attachment to only slightly ionizable or completely non-ionizable substances. Also, the use of adducts facilitates ionization through stabilizing fragile molecular ions which otherwise would fall apart during analysis thereby producing multiple fragments of substances of interest that may decrease the sensitivity to their detection.

The known techniques, however, use additives to bind with the parent molecules of explosives to create an adduct. The present disclosure has overcome the deficiencies of the prior art by shifting the signal of a sample of a substance of interest by complexing and reacting the sample with additives that react less efficiently with background signals and bind a dissociated ion portion of the sample to create an adduct that allows for identification of the sample of the substance of interest.

BRIEF DESCRIPTION OF THE DISCLOSURE

In one aspect of the present disclosure, a method for detecting a chemical substance is provided. The method includes collecting a sample of a substance of interest. The method also includes mixing the sample and at least one additive within a reaction chamber. The at least one additive includes at least one of an organic acid and an organic acid ester. The method also includes using an ionization source to produce an adduct from the sample and the at least one additive. The adduct includes the at least one additive and a dissociated ion from the sample. The method also includes performing a spectrometric analysis of the adduct. The method also includes identifying the sample using comparative spectrometric data.

In another aspect of the present disclosure, a substance detection system is provided. The system includes a reaction chamber housing defining a reaction chamber therein. The system also includes a sample supply system coupled in flow communication with said reaction chamber. The sample supply system is configured to channel at least a portion of a sample of interest to said reaction chamber. The system also includes an additive system coupled in flow communication with said reaction chamber. The additive system is configured to channel at least one additive to said reaction chamber. The at least one additive includes at least one of an organic acid and an organic acid ester. The system also includes an ionization source coupled in flow communication with said reaction chamber. The ionization source is configured to produce an adduct from the at least a portion of a sample of interest and the at least one additive including at least one of an organic acid and an organic acid ester. The adduct includes the at least one additive and a dissociated ion from the sample. The system also includes a spectrometric analysis device coupled in flow communication with said reaction chamber. The spectrometric analysis device is configured to perform a spectrometric analysis of the adduct. The system also includes a processor configured to identify at least one substance of interest using comparative spectrometric data.

In yet another aspect of the present disclosure, a method for distinguishing different $NO_3^-$ ion structures is provided. The method includes collecting a sample of a nitro-based substance. The method also includes mixing the sample and at least one additive within a reaction chamber. The at least one additive includes at least one of an organic acid and an organic acid ester. The method also includes using an ionization source to produce an adduct from the mixture of the sample and the at least one additive. The adduct includes the at least one additive and a dissociated $NO_3^-$ ion from the sample. The method also includes performing a spectrometric analysis of the adduct. The method also includes identifying the sample using comparative spectrometric data.

DETAILED DESCRIPTION OF THE DISCLOSURE

Figure 1A:
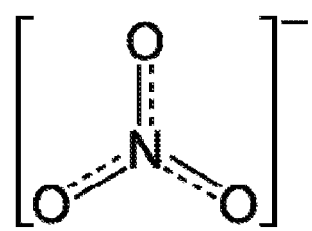
FIG. 1A is an exemplary embodiment of the planar trigonal structure of nitrate $NO_3^-$ in accordance with the present disclosure.

The embodiments disclosed herein improve detection of substances of interest (e.g., explosives) through selective ion chemistry. For example, this disclosure pertains to a method of using an additive to distinguish between two different ion structures for $NO_3^-$ arising from atmospheric air and from explosives (e.g., nitrate-based explosives) when using discharge and other types of ionization sources.

In one embodiment of the present disclosure, a method for detecting a chemical substance is disclosed. The method comprises collecting a sample of a substance of interest, mixing the sample and at least one additive within a reaction chamber, wherein the at least one additive includes at least one of an organic acid and an organic acid ester; using an ionization source to produce an adduct from the sample and the at least one additive, wherein the adduct includes the at least one additive and a dissociated ion from the sample; performing a spectrometric analysis of the adduct; and, identifying the sample using comparative spectrometric data.

In yet another embodiment of the present disclosure, a method for distinguishing different $NO_3^-$ ion structures is disclosed. The method comprises collecting a sample of a nitro-based substance; mixing the sample and at least one additive within a reaction chamber, wherein the at least one additive includes at least one of an organic acid and an organic acid ester; using an ionization source to produce an adduct from the mixture of the sample and the at least one additive, wherein the adduct includes the at least one additive and a dissociated $NO_3^-$ ion from the sample; performing a spectrometric analysis of the adduct; and, identifying the sample using comparative spectrometric data.

The substance of interest of the present disclosure can be any substance that is able to be identified through the methods of the present disclosure, including, for example, explosives, pollutants, narcotics, pesticides, chemical warfare agents, etc. In a preferred embodiment of the present disclosure, the substance of interest is a nitro-based substance, such as, for example, a nitro-based explosive. The nitro-based substance can comprise, without limitation, at least one of ammonium nitrate (AN), ammonium nitrate fuel oil (ANFO), urea nitrate (UN), trinitrotoluene (TNT), ethylene glycol dinitrate (EGDN), nitroglycerin (NG), pentaerythritol tetranitrate (PETN), high melting explosive (HMX) and Research Department Explosive (RDX). In some embodiments of the present disclosure, the substance of interest is ANFO.

The present disclosure includes two mechanisms that may be used to identify a substance of interest. First, an additive such as a carboxylic acid may bind with a dissociated ion from a substance of interest (such as a nitrate $NO_3^-$) to form an adduct. Alternatively, an additive comprising, for example, a carboxylate anion may be neutralized by a substance of interest (e.g., via nitric acid) to form a carboxylic acid and an ion from the substance of interest. In this mechanism, the substance of interest can be detected by the neutralization and therefore disappearance of the carboxylate anion. Both mechanisms can be used as effective indicators of the presence of a substance of interest. Further, regardless of the mechanism used to identify the presence of a substance of interest, the ratio of the adduct/carboxylate anion shows a strong enhancement in the presence of a substance of interest, such as a nitrate explosive. As such, this ratio can be an effective indicator of a substance of interest as well.

Figure 1B:
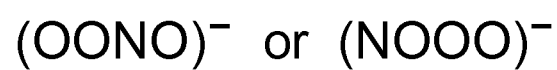
FIG. 1B is an exemplary embodiment of the two linear structures of atmospheric $NO_3^-$ in accordance with the present disclosure.

In some embodiments, the methods disclosed herein can distinguish between different $NO_3^-$ ion structures. In preferred embodiments, the $NO_3^-$ ion structures comprise at least one of nitrate $NO_3^-$ and atmospheric $NO_3^-$. Though often difficult to distinguish, nitrate $NO_3^-$ and atmospheric $NO_3^-$ have different structures and properties. For example, nitrate $NO_3^-$ has a planar trigonal structure, such as is shown in FIG. 1A. The nitrate $NO_3^-$ ion is the counter ion to nitric acid ($HNO_3$), which is a very strong acid. This, in turn, makes the nitrate $NO_3^-$ ion a weak base. Atmospheric $NO_3^-$, however, can be in the form of two linear structures of similar energy, such as shown in FIG. 1B.

Certain discharge sources, such as atmospheric pressure chemical ionization (APCI), create background air $NO_3^-$ ions that can interfere with nitrate $NO_3^-$ ions from substances of interest, such as explosives. ANFO, for example, gives a primarily nitrate $NO_3^-$ signal and therefore can be difficult to detect against the background atmospheric $NO_3^-$ signal. That is, the $NO_3^-$ ion signal from ANFO can be detected by mass spectrometry (MS) by monitoring $NO_3^-$, which has a mass-to-charge (m/z) ratio of (m/z 62), and $HNO_3NO_3^-$ with an m/z of (m/z 125). These signals, however, also occur for background air (i.e., atmospheric $NO_3^-$). Thus, the present disclosure provides for the ability to differentiate between atmospheric $NO_3^-$ and nitrate $NO_3^-$ that may come from an explosive substance of interest, such as, for example, ANFO.

The present disclosure provides for such a method by shifting the signal for nitrate $NO_3^-$ by complexing and reacting the nitrate $NO_3^-$ with additives that react much less efficiently with the background atmospheric $NO_3^-$ signal. For example, in some embodiments carboxylic acids may be complexed with nitrate $NO_3^-$ ions to identify a substance of interest.

In other embodiments, a mechanism is disclosed that involves the neutralization of carboxylates (i.e., $RCO_2^-$) by nitric acid to provide a reduction of the carboxylate signal ($RCO_2^-$) in the presence of a substance of interest (e.g., ANFO, UN). For example, a carboxylate mixed with nitric acid ($RCO_2^-+HNO_3$) can yield a carboxylic acid and nitrate $NO_3^-$ ($RCO_2H+NO_3^-$). The detection of substances of interest such as ANFO and UN may be further amplified by monitoring the ratio of complexation to neutralization for the adduct to the carboxylate anion, such as $RCO_2H$—$NO_3$ to $RCO_2^-$. One of the significant benefits of the mechanisms disclosed herein is that the methods can work with any class of acids, including both weak acids and strong acids.

The sample of the substance of interest may be obtained using a fresh sampling swab. The swab can be used to wipe the surface of the substance of interest to collect the sample of the substance of interest. Any quantity of substance of interest may be obtained as the sample so long as the sample includes enough of the substance of interest to allow for spectrometric analysis of the sample.

The method can include mixing the sample and at least one additive within a reaction chamber. The additive may also be contained on the sampling swab and be thermally desorbed along with the collected swab sample. In some embodiments, the at least one additive includes at least one of an organic acid and an organic acid ester. The at least one additive can comprise at least one of a carboxylic acid and a carboxylate. The carboxylic acids that can be used in the present disclosure include, but are not limited to, benzoic acid, oxalic acid and lactic acid. The carboxylates that can be used in the present disclosure include, but are not limited to, carboxylic acid esters. In some embodiments, the carboxylic acid ester comprises dicarboxylic acids, such as, for example, oxalic acid. In some embodiments, the carboxylic acid ester comprises an oxalic acid ester. In other embodiments, the carboxylic acid ester comprises an anion, such as, but not limited to, benzoic acid ester anion, lactic acid ester anion or oxalic acid ester anion.

In some embodiments of the present disclosure, the method includes mixing the sample and from about 1 nanogram to about 100 micrograms of the at least one additive. In other embodiments of the present disclosure, the sample can be mixed with from about 1 microgram to about 32 micrograms, from about 1 microgram to about 16 micrograms, from about 1 microgram to about 4 micrograms, about 4 micrograms, or about 1 microgram of the at least one additive.

In some embodiments, the method includes thermally desorbing the substances of interest and channeling those substances to the reaction chamber. Air can be pulled into a thermal desorption system through a first air intake. A first heating device and a second heating device can be energized to heat up and desorb the substances from a sampling swab. The desorbed substances can be entrained in the air flow and channeled to the reaction chamber for ionization.

The method can include using an ionization source to produce an adduct from the sample and the at least one additive, wherein the adduct includes the at least one additive and a dissociated ion from the sample. The ionization source can be any ionization system that enables operation of the methods and systems as described herein, including, without limitation, a radioactive ionization source, an electrospray ionization source (ESI), an atmospheric pressure chemical ionization (APCI) source, an atmospheric pressure photoionization (APPI) source, an atmospheric pressure glow discharge (APGD) source, a direct analysis in real time (DART) source, and an atmospheric pressure dielectric barrier discharge (APDBD) source. In some embodiments of the present disclosure, the ionization source comprises at least one of an APCI source, an APPI source, an ESI source and a DART source. Some embodiments of the present disclosure can be configured to operate at sub-atmospheric pressures. Such embodiments include an ionization source that can be, without limitation, a chemical ionization (CI) source, a photoionization (PI) source, a glow discharge (GD) source, and a dielectric barrier discharge (DBD) source.

The ionization source can produce an adduct from the sample and the at least one additive. The adduct comprises molecules of the at least one additive and molecules of the sample from combined molecules of additive and sample. In some embodiments, the adduct can include the at least one additive and a dissociated ion from the sample. For example, if the substance of interest is ANFO and the additive is benzoic acid, the benzoic acid can form an adduct with a dissociated nitrate ion from the ANFO (see, e.g., FIG. 5C). The present method not only provides for novel methods for an additive to bind with an explosive to attempt to identify the explosive substance, but, also, the present disclosure provides a novel method of binding an additive to a dissociated ("free") ion from a substance of interest to identify the substance of interest. The adduct ions may have either a negative polarity in the negative ion mode or a positive polarity in the positive ion mode. For each of the two polarities, the additives and the sample of the substance of interest are mixed in reaction chamber, thereby forming adducts.

Figure 2A:
FIG. 2A is an exemplary embodiment of the adduct formation of a dissociated nitrate ion and a carboxylic acid in accordance with the present disclosure.
Figure 2B:
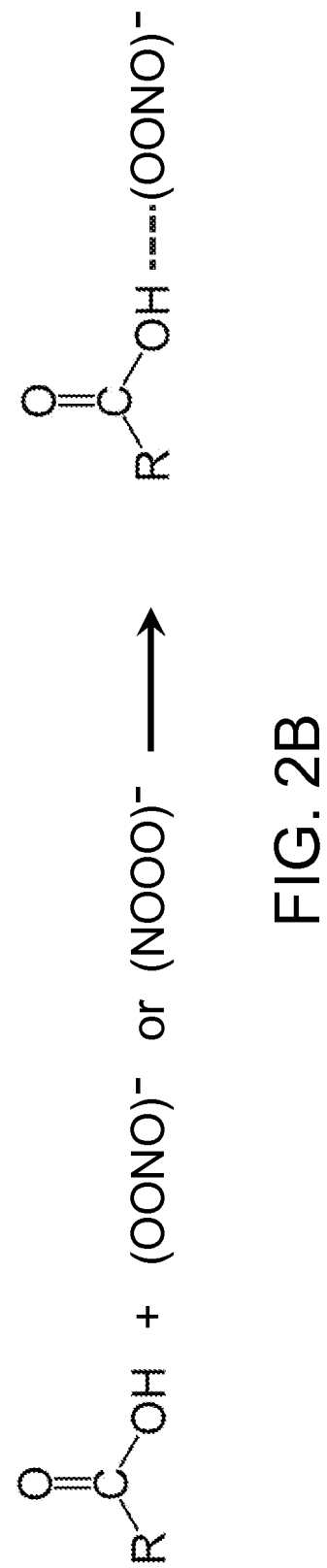
FIG. 2B is an exemplary embodiment of the adduct formation of an atmospheric $NO_3^-$ ion and a carboxylic acid in accordance with the present disclosure.

The methods disclosed herein are beneficial for distinguishing different $NO_3^-$ ion structures through the formation of adducts. For example, as shown in FIG. 2B, when a carboxylic acid is used as the additive, it weakly binds with atmospheric $NO_3^-$ and has a low abundance. When a carboxylic acid binds with a nitrate $NO_3^-$ ion, however, the adduct is strongly bound and is in high abundance (see, e.g., FIG. 2A). This is because nitrate $NO_3^-$ is the anion to nitric acid and has an affinity for protons. The linear structures of atmospheric $NO_3^-$ are not acid counter anions and thus have much less of an affinity for protons. The present disclosure has surprisingly found that the nitrate $NO_3^-$ anion can bind to a proton donor without actually abstracting the proton and forming a neutral nitric acid.

The methods disclosed herein can also include performing a spectrometric analysis of the adduct. The adduct ions can be channeled from the reaction chamber into a spectrometric analysis device for generating associated graphical representations of the determined mass spectrums. The methods disclosed herein can also include identifying the sample using comparative spectrometric data.

In other embodiments of the present disclosure, a substance detection system is disclosed. The substance detection system comprises a reaction chamber housing defining a reaction chamber therein; a sample supply system coupled in flow communication with said reaction chamber, said sample supply system configured to channel at least a portion of a sample of interest to said reaction chamber; an additive system coupled in flow communication with said reaction chamber, said additive system configured to channel at least one additive to said reaction chamber, wherein the at least one additive includes at least one of an organic acid and an organic acid ester; an ionization source coupled in flow communication with said reaction chamber, said ionization source configured to produce an adduct from the at least a portion of a sample of interest and the at least one additive including at least one of an organic acid and an organic acid ester, wherein the adduct includes the at least one additive and a dissociated ion from the sample; a spectrometric analysis device coupled in flow communication with said reaction chamber, said spectrometric analysis device configured to perform a spectrometric analysis of the adduct; and, a processor configured to identify at least one substance of interest using comparative spectrometric data.

Figure 10:
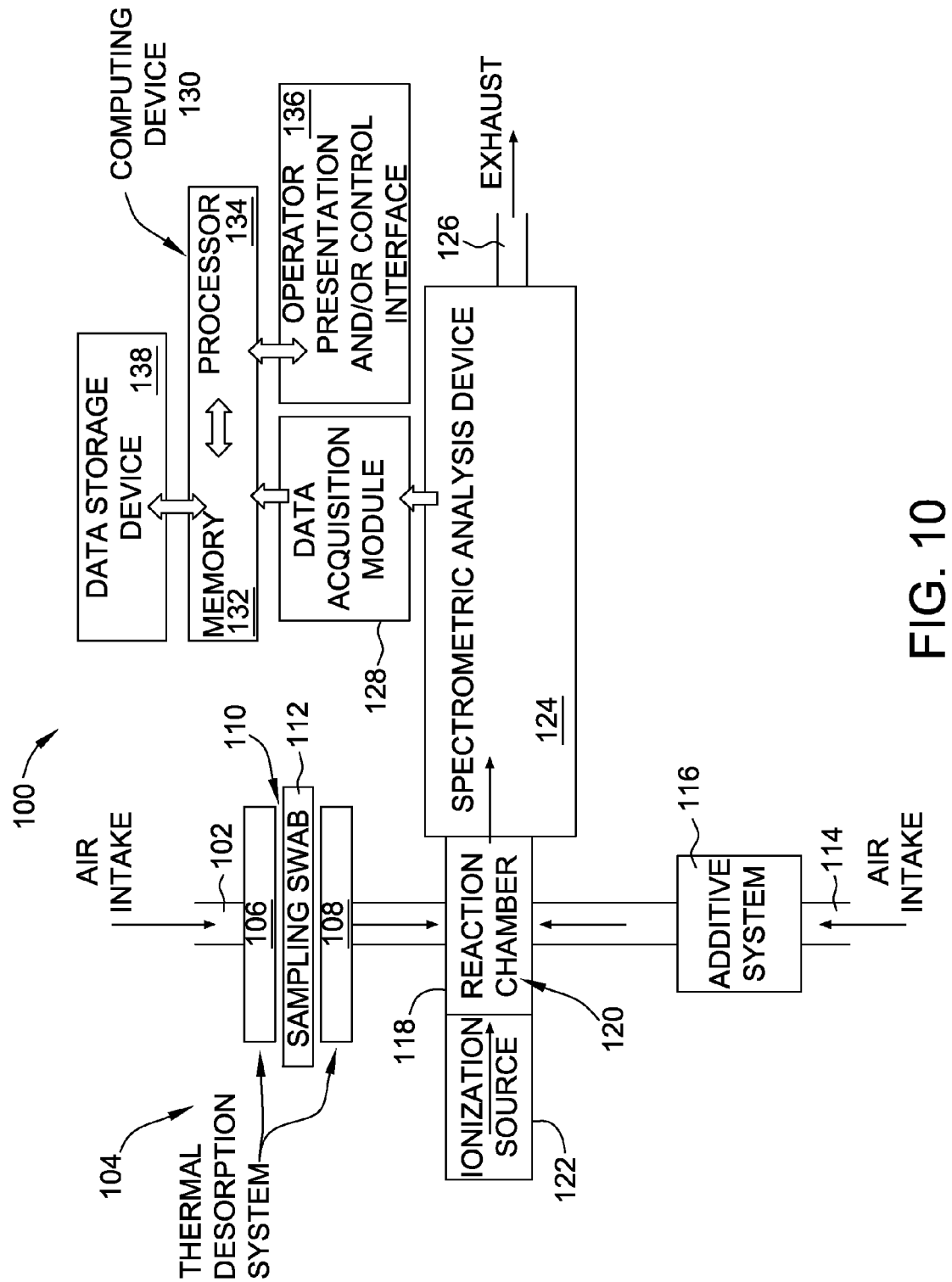
FIG. 10 is an exemplary schematic view of a substance detection system in accordance with the present disclosure.

FIG. 10 is a schematic view of an exemplary substance detection system 100. In the exemplary embodiment, system 100 includes a first air intake device 102. System 100 also includes a sample supply system, i.e., such as a thermal desorption system 104 coupled in flow communication with first air intake device 102. Thermal desorption system 104 further includes a first heating device 106 and a second heating device 108 that define a sampling swab insertion port 110 that receives a sampling swab 112. Alternatively, any configuration of the thermal desorption system 104 that enables operation of system 100 as described herein can be used. In the exemplary embodiment, substance detection system 100 further includes a second air intake device 114 and an additive system 116 coupled in flow communication with second air intake device 114. System 100 further includes a reaction chamber housing 118 defining a reaction chamber 120 coupled in flow communication with thermal desorption system 104 and additive system 116.

In the exemplary embodiment, system 100 also includes an ionization source 122 coupled in flow communication with reaction chamber 120. Ionization source 122 can be any ionization system that enables operation of system 100 as described herein. Substance detection system 100 further includes a spectrometric analysis device 124 coupled in flow communication with reaction chamber 120. In the exemplary embodiment, spectrometric analysis device 124 is a single quadrupole mass spectrometry device. In alternative embodiments, spectrometric analysis device 124 is any spectrometric analysis system that enables operation of system 100 as described herein, including, without limitation, any mass spectrometry device, any ion mobility spectrometry device, and any differential ion mobility spectrometry device. System 100, in the exemplary embodiment, also includes an exhaust device 126 coupled in flow communication with the spectrometric analysis device 124.

In the exemplary embodiment, substance detection system 100 also includes a data acquisition module 128 coupled to spectrometric analysis device 124. System 100 further includes a computing device 130 coupled to data acquisition module 128. Computing device 130 performs spectrometric analyses of the spectrum data imported from data acquisition module 128. In alternative embodiments, computing device 130 also facilitates control of spectrometric analysis device 124, data acquisition module 128, and any other apparatus associated with substance detection system 100.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

In one embodiment, computing device 130 includes a memory device 132 and a processor 134 operatively coupled to the memory device 132 for executing instructions. In some embodiments, executable instructions are stored in the memory device 132. Computing device 130 is configurable to perform one or more operations described herein by the programming processor 134. For example, processor 134 may be programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 may include one or more computer readable media.

Memory device 132 may be configured to store operational measurements including, without limitation, real-time and historical spectrometric data including, without limitation, sample identification using comparative spectrometric data, isotopic ratios of molecular adduct ions and fragment adduct ions, timing data of elution profiles, thermal desorption profiles, and chromatographic elution profiles for isotopes of adduct ions, and data on ratios of isotopic adduct ions, e.g., relative intensities of isotopic peaks and peak areas of adduct ions in a spectrum, and/or any other type data.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

In the exemplary embodiment, computing device 130, including memory device 132, includes, without limitation, sufficient computer-readable/executable instructions, sufficient data and data structures, algorithms, and commands to facilitate generating comparisons of the data imported from data acquisition module 128 with the stored historical spectrometric data described above. In addition, computing device 130 can either include, or is coupled to, a data storage device 138 that is configured to store such computer-readable/executable instructions, historical data and data structures, algorithms, and commands.

In the exemplary embodiment, substance detection system 100 further includes an operator presentation and/or control interface 136 coupled to computing device 130. Interface 136 presents data, such as spectrometric comparison data to a user (not shown). In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, substance detection system 100 may be networked with other systems and devices such that data transmitted across portions of system 100 may be accessed by any device capable of accessing computing device 130 including, without limitation, desktop computers, laptop computers, and personal digital assistants (PDAs) (neither shown).

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Example 1 examined the effectiveness of benzoic acid as an additive to identify a substance of interest in accordance with the methods and systems of the present disclosure. Benzoic acid ($C_6H_5COOH$) is an acid that is capable of complexing without dissociating. Benzoic acid is non-volatile, non-toxic and stable, and, as such, has a long shelf-life if dosed on swabs or inserted into a dopant system. A quadrupole ion trip, time of flight (QIT TOF) mass spectrometer was used as the APCI source for carrying out the method of Examples 1-4.

In Example 1, ANFO was used as the substance of interest and benzoic acid was used as the additive. A trial including 100 nanograms of the ANFO sample and 4 micrograms of the benzoic acid were mixed in a reaction chamber using the APCI source to produce an adduct including benzoic acid and a dissociated (i.e., free) nitrate $NO_3^-$ ion. A spectrometric analysis was then performed on the adduct using the mass spectrometer and the results of the trial are shown in FIG. 3A.

Additionally, a separate trial was run using 4 micrograms of benzoic acid in the APCI source, however, no ANFO was added to this trial. In this trial, the benzoic acid binds with the linear structure of the background atmospheric $NO_3^-$. The results of the spectrometric analysis of this trials are shown in FIG. 3B.

Figure 3A:
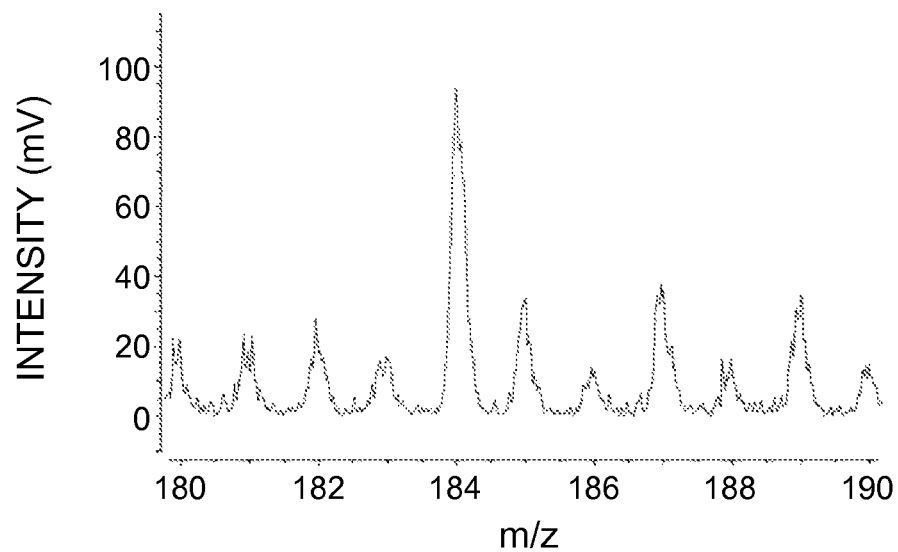
FIG. 3A is an exemplary embodiment of a spectrometric analysis of an ANFO signal with an adduct comprising benzoic acid and nitrate $NO_3^-$ in accordance with the present disclosure.
Figure 3B:
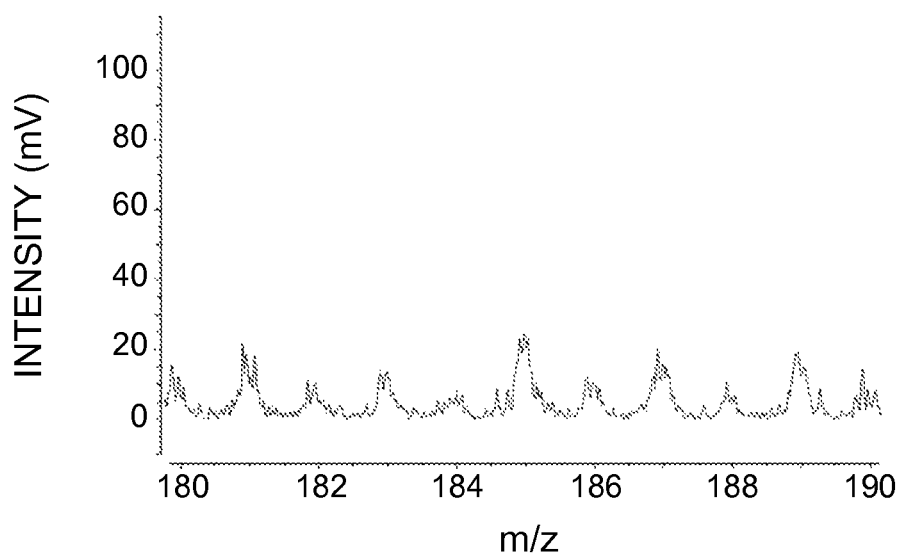
FIG. 3B is an exemplary embodiment of a spectrometric analysis of an ANFO signal with an adduct comprising benzoic acid and atmospheric $NO_3^-$ in accordance with the present disclosure.

As can be seen in FIG. 3A, a signal for nitrate $NO_3^-$ appears at m/z 184, which indicates the presence of nitrate $NO_3^-$ from the explosive ANFO. Conversely, even though the benzoic acid binds with the atmospheric $NO_3^-$ from the APCI source, the signal for $NO_3^-$ does not appear in FIG. 3B. Thus, Example 1 shows that the adduct including benzoic acid and the dissociated nitrate $NO_3^-$ ion is an effective indicator of ANFO because the nitrate can be detected while the atmospheric $NO_3^-$ is not. When compared to the spectrometric data evidenced for atmospheric $NO_3^-$, one skilled in the art can identify whether or not a particular substance of interest (such as ANFO) is present in the sample.

Figure 4:
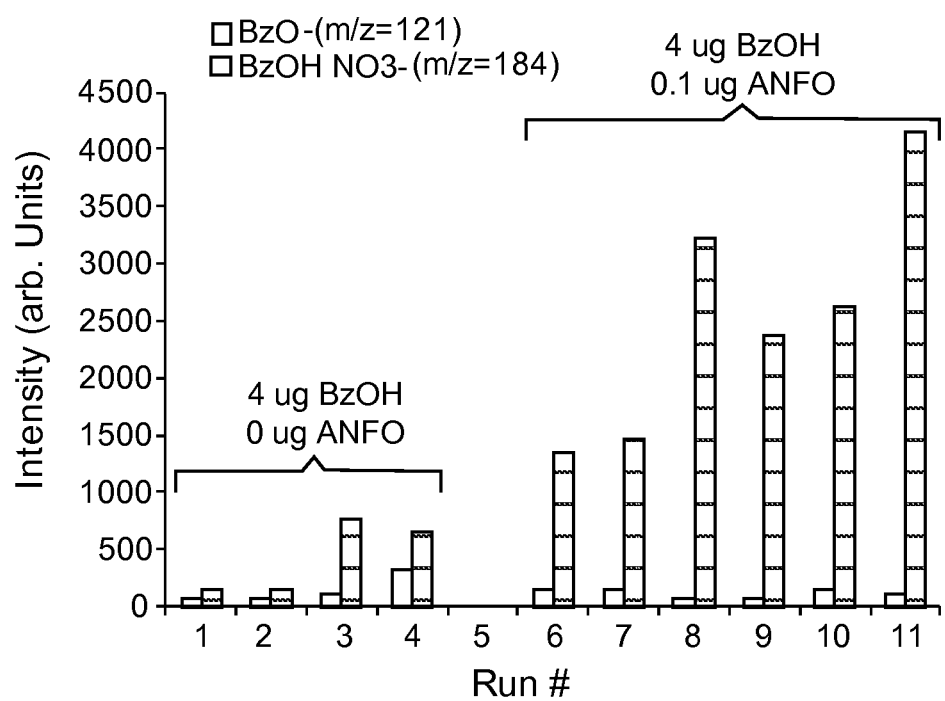
FIG. 4 is an exemplary graph depicting the effectiveness of an adduct including benzoic acid and nitrate $NO_3^-$ as an indicator of ANFO in accordance with the present disclosure.

Furthermore, FIG. 4 also provides evidence that the benzoic acid/$NO_3^-$ adduct is an effective indicator of ANFO. For trial runs 1-4, 4 micrograms of benzoic acid were used in the APCI source while there was no ANFO present. For trial runs 6-11, 4 micrograms of benzoic acid were combined with 0.1 micrograms of ANFO, which showed indications of the m/z 184 signal in each run. The limit of detection (LOD) ($3\sigma$) for the trial runs was 47 nanograms. Thus, the results shown in FIG. 4 provide further evidence that the benzoic acid/$NO_3^-$ adduct is an effective indicator of ANFO.

Example 2

Figure 5A:
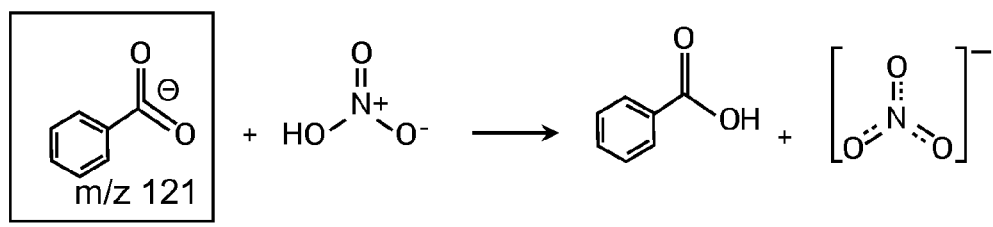
FIG. 5A is an exemplary embodiment of the formation of benzoic acid and nitrate $NO_3^-$ from a benzoic acid carboxylate anion ($BzO^-$) and $HNO_3$ in accordance with the present disclosure.

Example 2 compared the different ion signals for benzoic acid and a carboxylate—benzoic acid anion ($C_6H_5CO_2^-$)—in accordance with the present disclosure. FIG. 5A depicts an exemplary embodiment of the formation of benzoic acid and nitrate $NO_3^-$ from the combination of benzoic acid anion (m/z 121) and nitric acid ($HNO_3$) as used in an APCI source in accordance with the present disclosure. Nitric acid is formed as a byproduct of the thermal desorption of AN or ANFO. FIG. 5C depicts an exemplary embodiment of the formation of an adduct including benzoic acid and nitrate $NO_3^-$ (m/z 184) from the combination of benzoic acid and a dissociated nitrate $NO_3^-$ ion as used in an APCI source in accordance with the present disclosure.

Figure 5B:
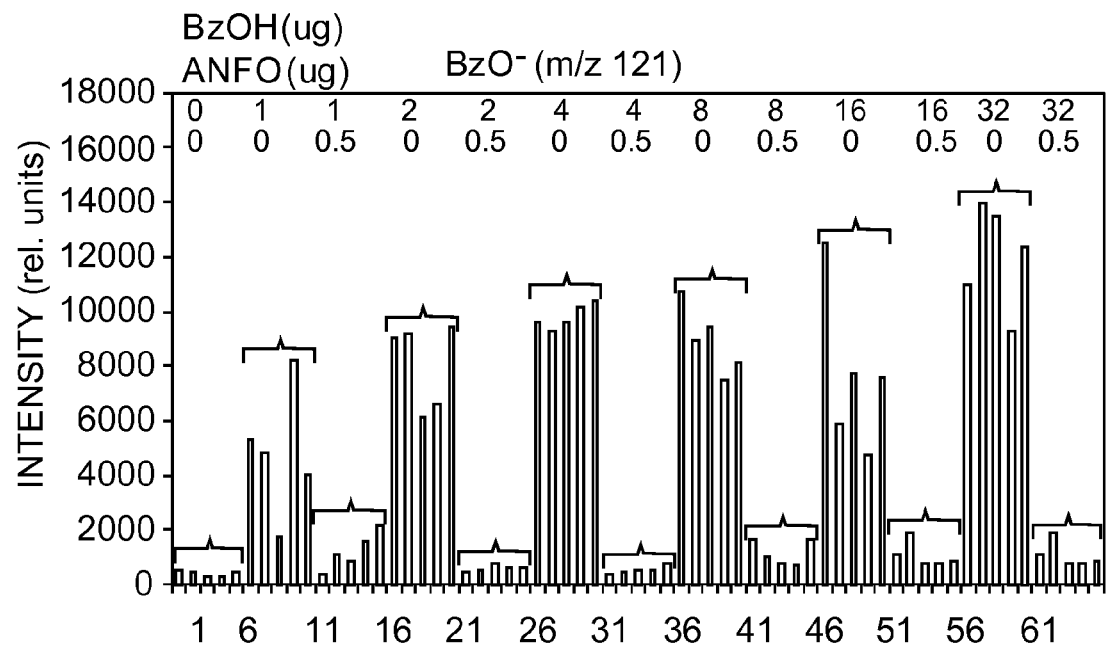
FIG. 5B is an exemplary graph depicting the effectiveness of BzO⁻ as an indicator of the presence of ANFO in accordance with the present disclosure.
Figure 5C:
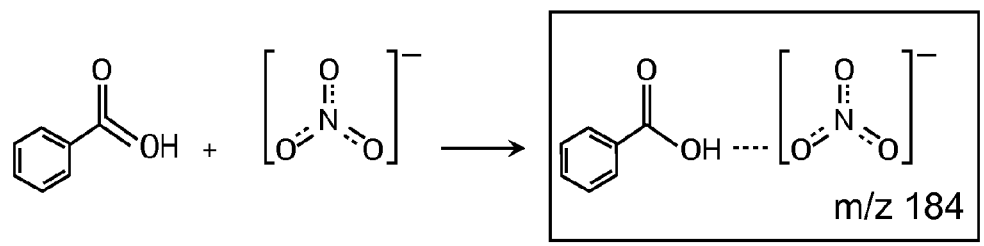
FIG. 5C is an exemplary embodiment of the formation of an adduct including benzoic acid (BzOH) and nitrate $NO_3^-$ in accordance with the present disclosure.

For each ion signal, the following additions of benzoic acid and ANFO were added over the course of 13 separate experimental trials (each trial included 5 runs each at the disclosed amounts, as indicated by the brackets in FIG. 5B):

TABLE 1

| Benzoic Acid (micrograms) | ANFO (micrograms) |
| --- | --- |
| 0 | 0 |
| 1 | 0 |
| 1 | 0.5 |
| 2 | 0 |
| 2 | 0.5 |
| 4 | 0 |
| 4 | 0.5 |
| 8 | 0 |
| 8 | 0.5 |
| 16 | 0 |

TABLE 1-continued

| Benzoic Acid (micrograms) | ANFO (micrograms) |
|---|---|
| 16 | 0.5 |
| 32 | 0 |
| 32 | 0.5 |

Figure 5D:
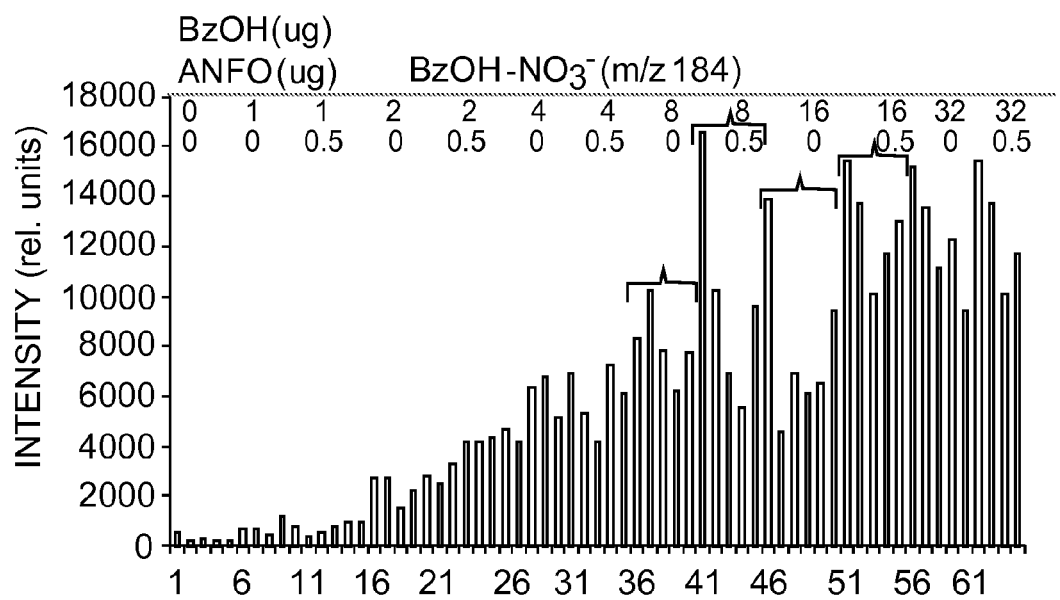
FIG. 5D is an exemplary graph depicting the effectiveness of a BzOH—$NO_3^-$ adduct as an indicator of the presence of ANFO in accordance with the present disclosure.

As shown in FIG. 5B, the benzoic acid anion (benzoate) shows a strong attenuation in the presence of ANFO, which can be correlated to the reaction with the $HNO_3$ of ANFO. As shown in FIG. 5D, the m/z 184 peaks are prevalent when the ANFO is added; however, this differentiation is not as pronounced as is the benzoate anion attenuation, which is due to benzoic acid being a relatively weak acid (the brackets in FIG. 5D indicate a series of 5 runs for a particular trial amount). Thus, Example 2 indicates that both benzoic acid and benzoate anion are effective indicators of ANFO, either through the formation of a benzoic acid/$NO_3^-$ adduct or in the absence of the benzoic acid anion when ANFO is present.

Figure 6A:
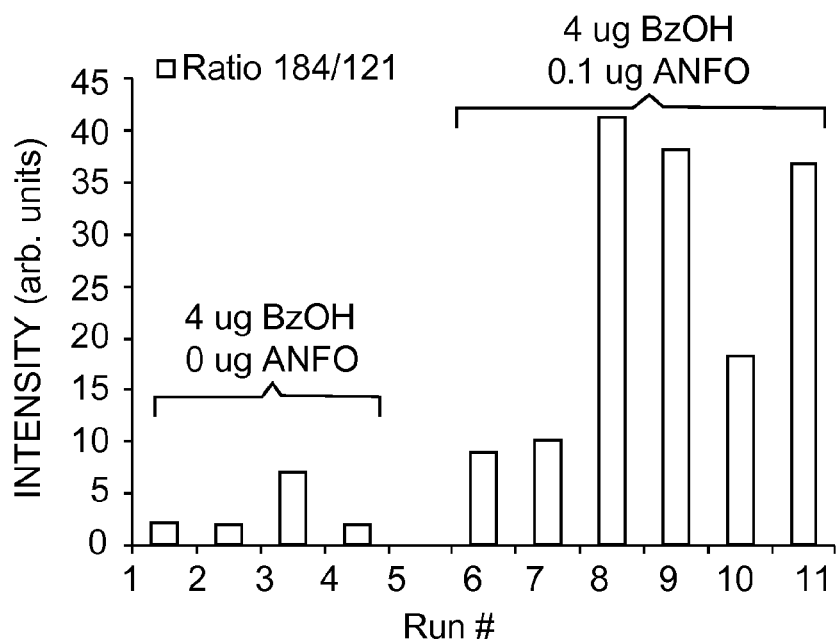
FIG. 6A is an exemplary graph depicting the ratio of BzOH—$NO_3^-$ to BzO⁻ in accordance with the present disclosure.

Furthermore, the present disclosure shows that the ratio of the benzoic acid/$NO_3^-$ adduct (m/z 184) to the benzoate anion (m/z 121) is also an effective indicator of the presence of ANFO. FIG. 6A depicts the ratio of the benzoic acid/$NO_3^-$ adduct to the benzoate anion when 4 micrograms of benzoic acid were used in the APCI source while there was no ANFO present (trial runs 1-4) and when 4 micrograms of benzoic acid were combined with 0.1 micrograms of ANFO (trial runs 6-11). The limit of detection (LOD) ($3\sigma$) for the trial runs was 33 nanograms.

Figure 6B:
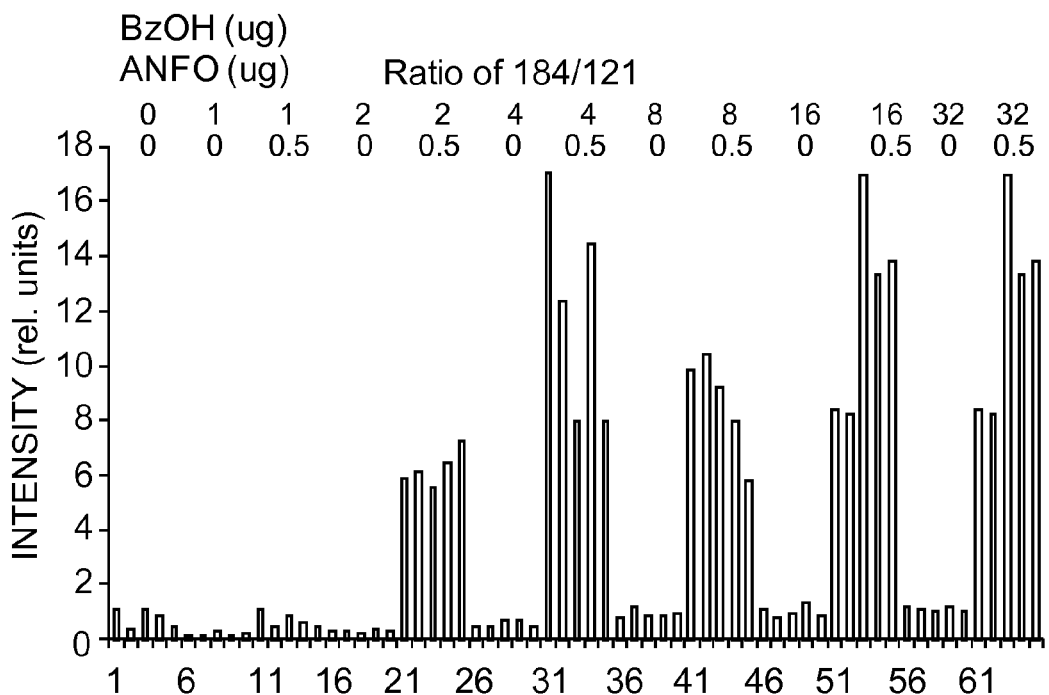
FIG. 6B is an exemplary graph depicting the ratio of BzOH—$NO_3^-$ to BzO⁻ as an effective indicator of the presence of ANFO in accordance with the present disclosure.

Similarly, FIG. 6B depicts the ratio of m/z 184 to m/z 121 over the course of the 13 trial runs disclosed in Table 1. The limit of detection (LOD) ($3\sigma$) for the trial runs was 14 nanograms. As can be seen in FIG. 6B, the ratio of 184/121 is an effective indicator ANFO. The use of the ratio is very effective because it is responsive to either or both of the adduct formation of benzoic acid (or any organic acid or organic acid ester in general) with nitrate ion and the neutralization of benzoate anion (or any anion of an organic acid or organic acid ester). The efficiency of these reactions is dependent on the acidity of the acid such that stronger acids favor the former reaction and weaker acids favor the latter reaction.

Example 3

Figure 7A:
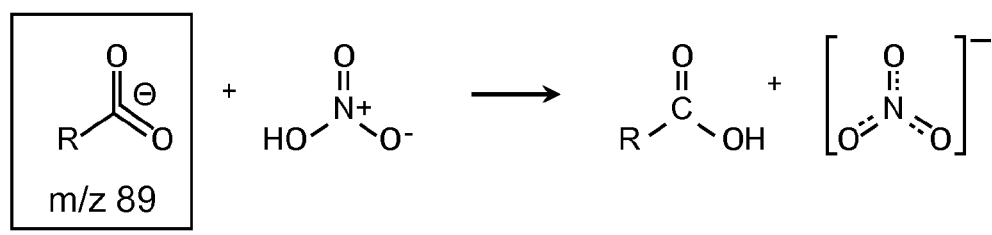
FIG. 7A is an exemplary embodiment of the formation of oxalic acid and nitrate $NO_3^-$ from an oxalic acid carboxylate anion (OxO⁻) and $HNO_3$ in accordance with the present disclosure.

Example 3 examined the effectiveness of oxalic acid ($H_2C_2O_4$) and a carboxylate oxalic acid anion ($HC_2O_4^-$) as indicators of ANFO. FIG. 7A depicts an exemplary embodiment of the formation of oxalic acid (wherein R=$HCO_2$) and nitrate $NO_3^-$ from the combination of oxalic acid anion (wherein R=$HCO_2$) (m/z 89) and nitric acid as used in an APCI source in accordance with the present disclosure. FIG. 7C depicts an exemplary embodiment of the formation of an adduct including oxalic acid (wherein R=$HCO_2$) and nitrate $NO_3^-$ (m/z 152) from the combination of oxalic acid (wherein R=$HCO_2$) and a dissociated nitrate $NO_3^-$ ion as used in an APCI source in accordance with the present disclosure.

Figure 7B:
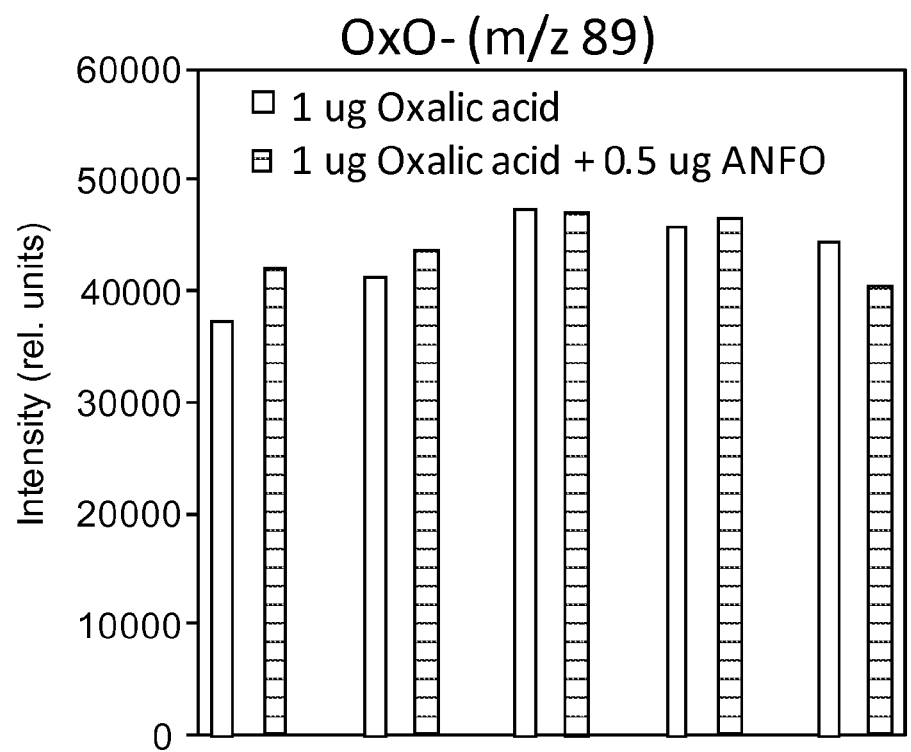
FIG. 7B is an exemplary graph depicting the effectiveness of OxO⁻ as an indicator of the presence of ANFO in accordance with the present disclosure.
Figure 7C:
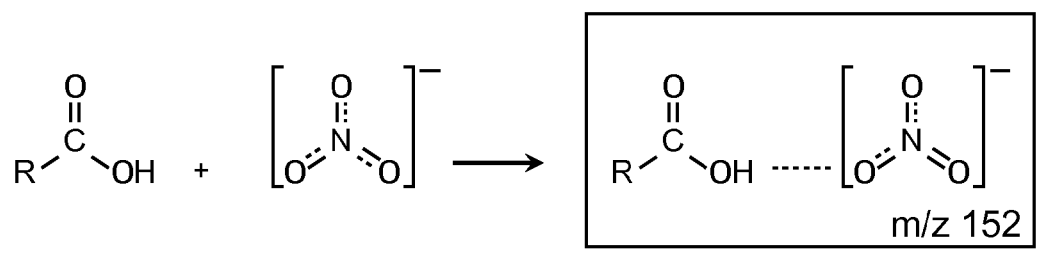
FIG. 7C is an exemplary embodiment of the formation of an adduct including oxalic acid (OxOH) and nitrate $NO_3^-$ in accordance with the present disclosure.

FIG. 7B shows the spectrometric analysis of the oxalic acid anion (m/z 89) signal in the presence of 1 microgram of oxalic acid and in the presence of the combination of 1 microgram of oxalic acid and 0.5 micrograms of ANFO. As can be seen in FIG. 7B, the oxalic acid anion (oxalate) does not show an attenuation in the presence of ANFO. This is in contrast to the benzoic acid anion discussed in Example 2, because oxalic acid is a stronger acid than benzoic acid and therefore the oxalate anion prefers to remain dissociated from the proton from nitric acid.

Figure 7D:
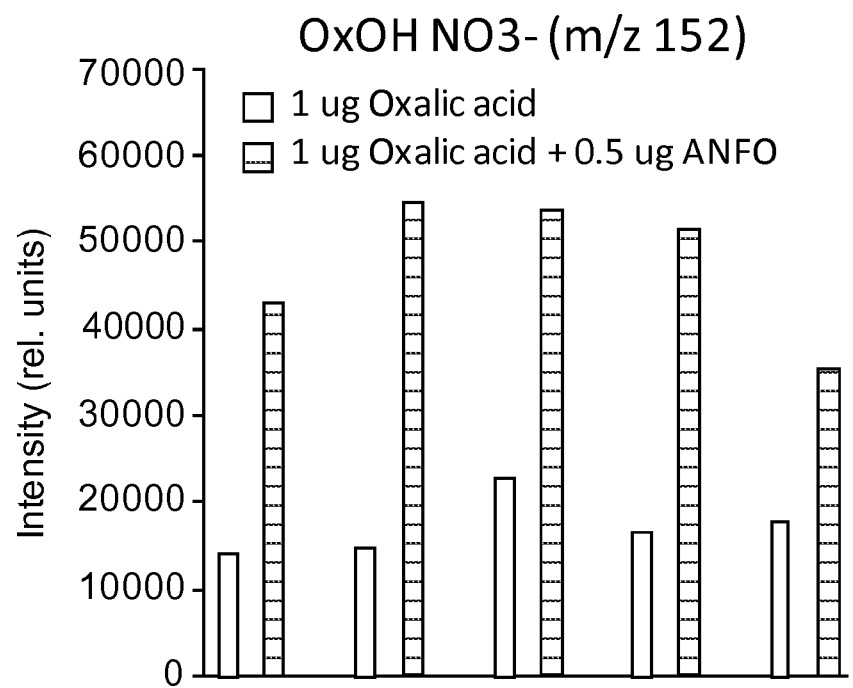
FIG. 7D is an exemplary graph depicting the effectiveness of an OxOH-$NO_3^-$ adduct as an indicator of the presence of ANFO in accordance with the present disclosure.

FIG. 7D shows the spectrometric analysis of the signal from the adduct including oxalic acid and nitrate $NO_3^-$ (m/z 152) in the presence of 1 microgram of oxalic acid and in the presence of the combination of 1 microgram of oxalic acid and 0.5 micrograms of ANFO. As can be seen in FIG. 7D, the adduct including oxalic acid and nitrate $NO_3^-$ (m/z 152) is an effective indicator of ANFO. Additionally, FIG. 7D indicates that oxalic acid complexes more strongly to nitrate $NO_3^-$ than does benzoic acid, as expected because oxalic acid is a stronger acid than benzoic acid.

Figure 7E:
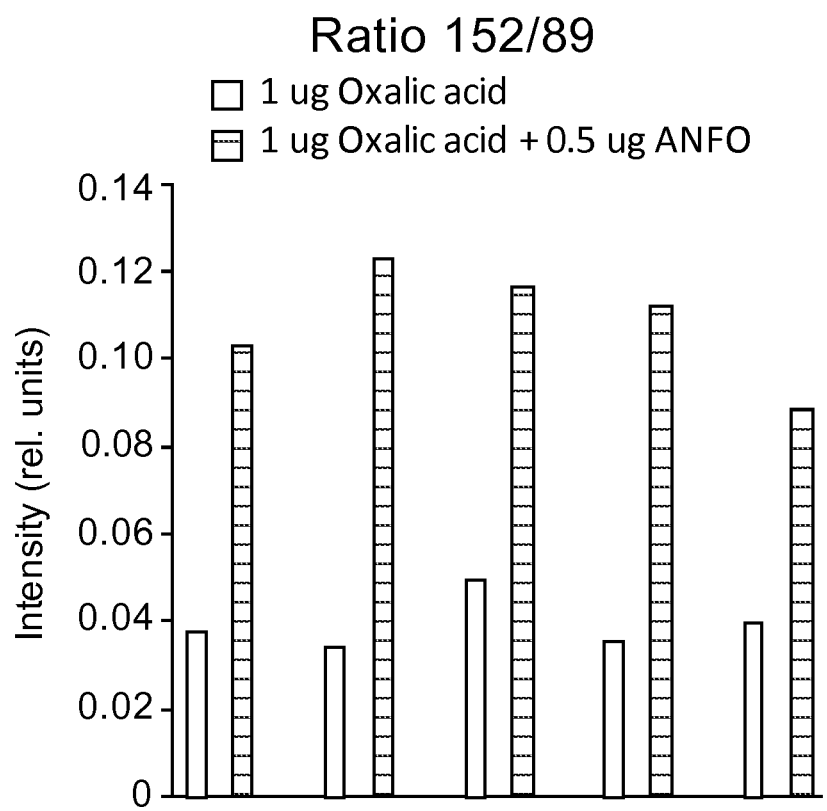
FIG. 7E is an exemplary graph depicting the ratio of OxOH-$NO_3^-$ to OxO⁻ as an effective indicator of the presence of ANFO in accordance with the present disclosure.

FIG. 7E depicts the ratio of the oxalic acid/nitrate $NO_3^-$ adduct (m/z 152) to the oxalic acid anion (m/z 89) in the presence of 1 microgram of oxalic acid and in the presence of the combination of 1 microgram of oxalic acid and 0.5 micrograms of ANFO. The ratio of 152/89 gave a limit of detection ($3\sigma$) of 110 nanograms.

Example 4

Figure 8A:
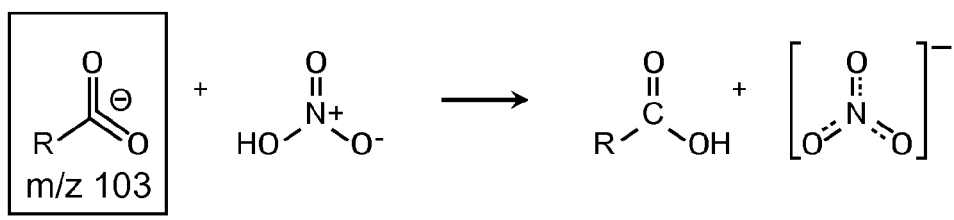
FIG. 8A is an exemplary embodiment of the formation of an oxalic acid ester and nitrate $NO_3^-$ from an oxalate ester anion and $HNO_3$ in accordance with the present disclosure.

Example 4 examined the effectiveness of an oxalic acid ester anion (oxalate ester) in an APCI source as an effective indicator of ANFO. FIG. 8A depicts an exemplary embodiment of the formation of an oxalic acid ester (wherein R=$COOCH_2CH_3$) and nitrate $NO_3^-$ from the combination of an oxalic acid ester anion (wherein R=$COOCH_2CH_3$)(m/z 103) and nitric acid as used in an APCI source in accordance with the present disclosure. FIG. 8C depicts an exemplary embodiment of the formation of an adduct including an oxalic acid ester (wherein R=$COOCH_2CH_3$) and nitrate $NO_3^-$ (m/z 166) from the combination of an oxalic acid ester (wherein R=$COOCH_2CH_3$) and a dissociated nitrate $NO_3^-$ ion as used in an APCI source in accordance with the present disclosure.

Figure 8B:
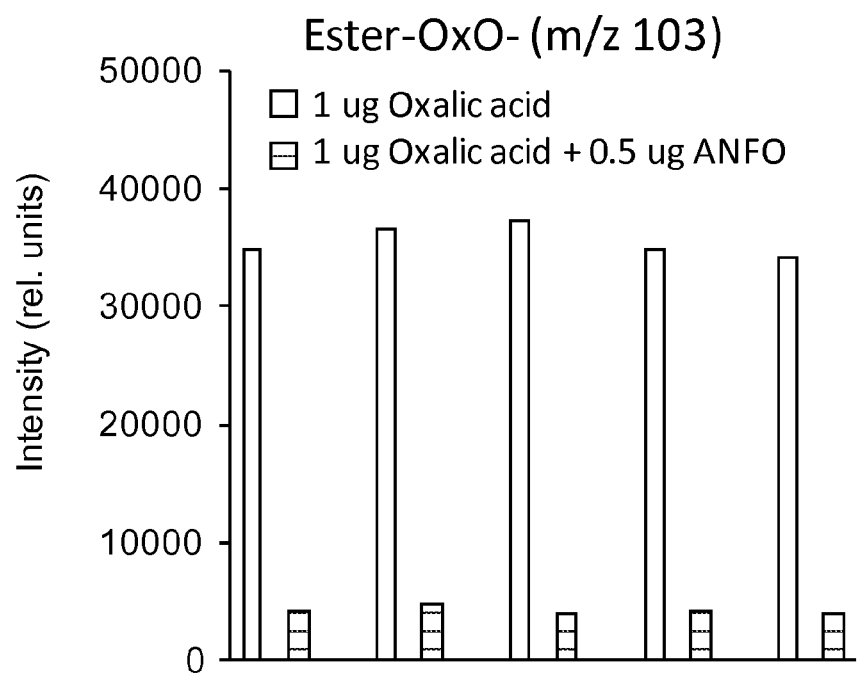
FIG. 8B is an exemplary graph depicting the effectiveness of an oxalate ester anion as an indicator of the presence of ANFO in accordance with the present disclosure.
Figure 8C:
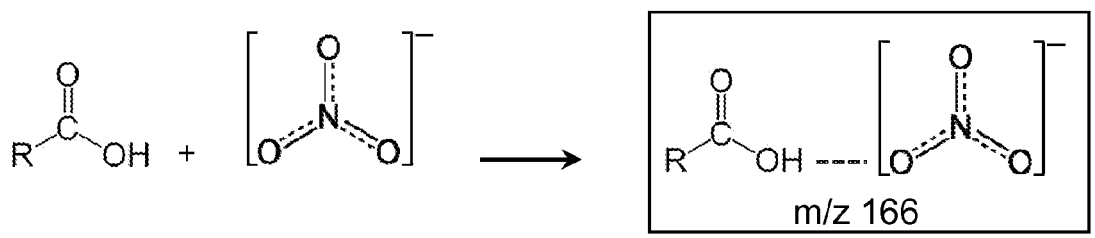
FIG. 8C is an exemplary embodiment of the formation of an adduct including oxalic acid ester and nitrate $NO_3^-$ in accordance with the present disclosure.

FIG. 8B shows the spectrometric analysis of the oxalate ester anion (m/z 103) signal in the presence of 1 microgram of oxalic acid and in the presence of the combination of 1 microgram of oxalic acid and 0.5 micrograms of ANFO. As can be seen in FIG. 8B, the oxalate ester anion peak shows strong attenuation in the presence of ANFO, indicating that the ester form of the oxalate anion is a weaker acid version of the unesterified oxalate anion, as expected for a monocarboxylic acid versus a dicarboxylic acid. FIG. 8B also indicates that the attenuation of the oxalate ester anion is an effective indicator of the presence of ANFO.

Example 5

Figure 9A:
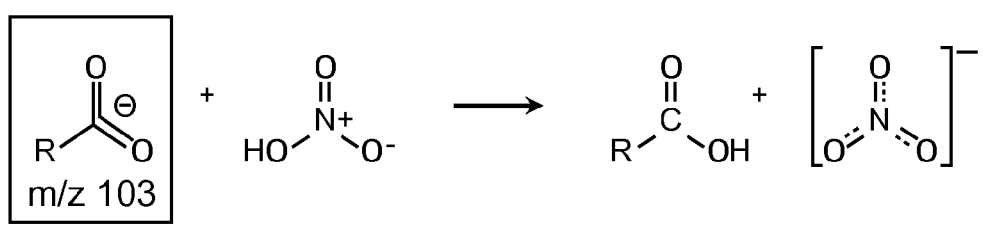
FIG. 9A is another exemplary embodiment of the formation of oxalic acid ester and nitrate $NO_3^-$ from an oxalate ester anion and $HNO_3$ in accordance with the present disclosure.

Example 5 examined the effectiveness of an oxalate ester anion in an APPI source as an effective indicator of ANFO. FIG. 9A depicts an exemplary embodiment of the formation of an oxalic acid ester (wherein R=$COOCH_2CH_3$) and nitrate $NO_3^-$ from the combination of an oxalate ester anion (wherein R=$COOCH_2CH_3$)(m/z 103) and nitric acid as used in an APPI source in accordance with the present disclosure. FIG. 9C depicts an exemplary embodiment of the formation of an adduct including an oxalic acid ester (wherein R=$COOCH_2CH_3$) and nitrate $NO_3^-$ (m/z 166) from the combination of an oxalic acid ester (wherein R=$COOCH_2CH_3$) and a dissociated nitrate $NO_3^-$ ion (m/z 62) as used in an APPI source in accordance with the present disclosure.

Figure 9B:
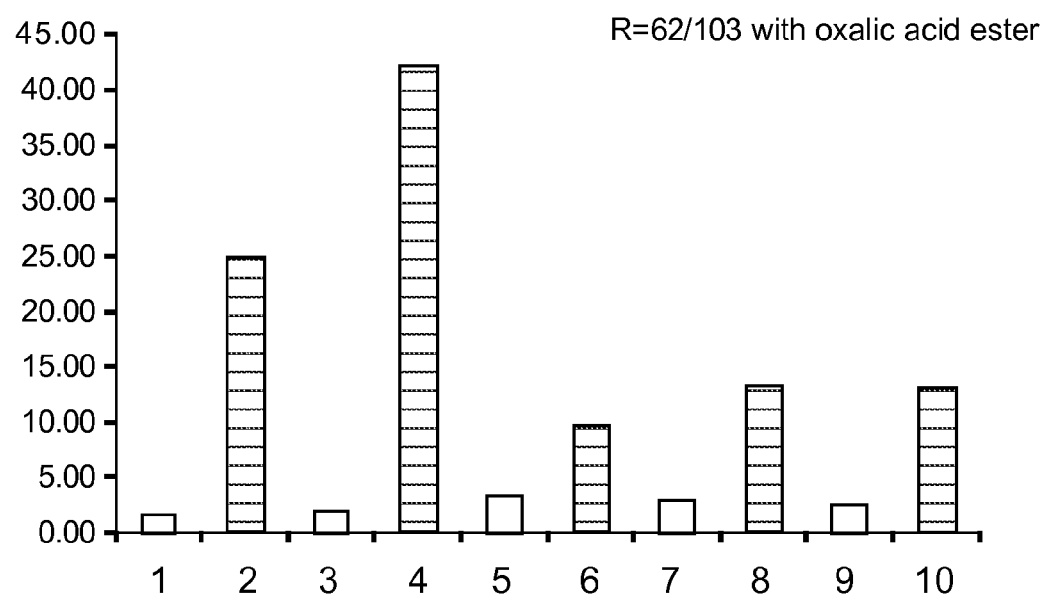
FIG. 9B is an exemplary graph depicting the ratio of nitrate $NO_3^-$ to oxalate ester anion as an effective indicator of the presence of ANFO through an atmospheric pressure photo ionization (APPI) source in accordance with the present disclosure.
Figure 9C:
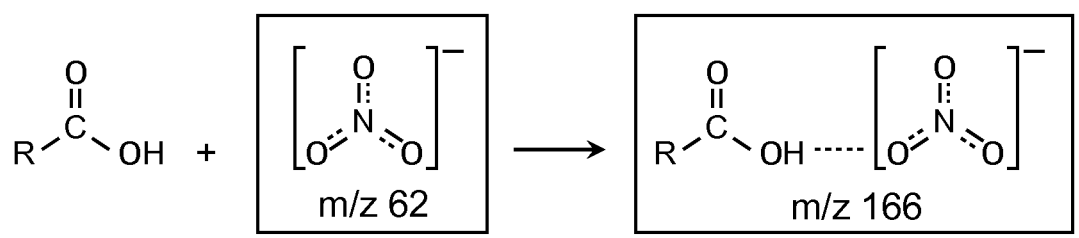
FIG. 9C is another exemplary embodiment of the formation of an adduct including OxOH-$NO_3^-$ in accordance with the present disclosure.
Figure 9D:
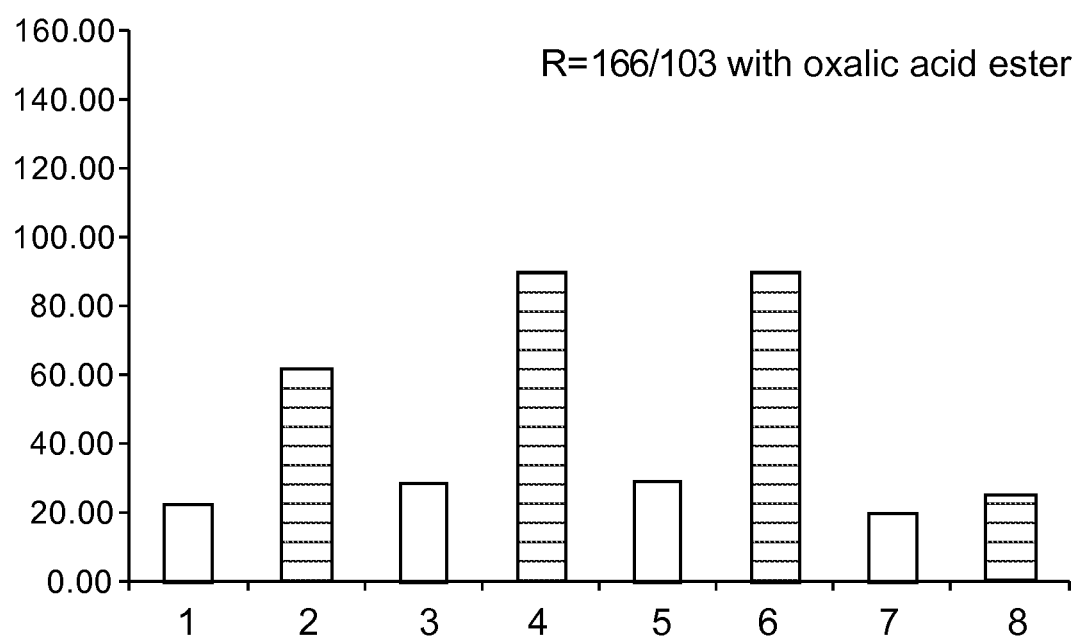
FIG. 9D is another exemplary graph depicting the ratio of nitrate $NO_3^-$ to oxalate ester anion as an effective indicator of the presence of ANFO through an atmospheric pressure photo ionization (APPI) source in accordance with the present disclosure.

FIG. 9B shows the ratio of the nitrate $NO_3^-$ ion (m/z 62) to the oxalate ester anion (m/z 103) in the presence of an oxalic acid ester. FIG. 9D shows the ratio of the oxalic acid ester adduct (m/z 166) to the oxalate ester anion (m/z 103) without the presence of an oxalic acid ester. The increase of the m/z 62 signal due to the presence of ANFO is greater than the decrease of the signal due to complexation. These results indicate that for an APPI source, there is much less atmospheric $NO_3"$ and thus the m/z 62 signal is mostly due to nitrate $NO_3^-$, which alone is suitable for nitrate detection. The sensitivity can also be enhanced by also using the m/z 103 oxalate ester anion in a ratio of m/z 62/103 as well as the ratio of the oxalic acid ester adduct (m/z 166) to the oxalate ester anion (m/z 103). The ratio of m/z 62/103 gave a limit of detection ($3\sigma$) of 15 nanograms and the ratio of 166/103 gave a limit of detection ($3\sigma$) of 5 nanograms in the presence of the oxalic acid ester.

In accordance with the systems and methods of the present disclosure, Examples 1-5 show that two mechanisms may be used to identify a substance of interest, such as ANFO. First, a carboxylic acid may bind with a dissociated nitrate ion to form an adduct. Alternatively, a carboxylate anion may be neutralized by nitric acid to form a carboxylic acid and a nitrate ion. Both mechanisms can be used as effective indicators of the presence of a substance of interest. Further, regardless of the mechanism used to identify the presence of a substance of interest, the ratio of the adduct/carboxylate anion shows a strong enhancement in the presence of a substance of interest, such as a nitrate explosive.

Exemplary embodiments of substance detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting a chemical substance, said method comprising:
   collecting a sample comprising a substance of interest;
   mixing the sample and at least one additive within a reaction chamber, wherein the at least one additive includes at least one of an organic acid and an organic acid ester;
   using an ionization source to produce an adduct from the sample and the at least one additive, wherein the adduct includes the at least one additive and a dissociated ion from the sample;
   performing a spectrometric analysis of the adduct; and,
   identifying the substance of interest using spectrometric data.

2. The method of claim 1, wherein the at least one additive comprises at least one of a carboxylic acid and a carboxylate.

3. The method of claim 2, wherein the carboxylic acid comprises at least one of benzoic acid, oxalic acid, and lactic acid.

4. The method of claim 2, wherein the carboxylate is a carboxylic acid ester.

5. The method of claim 1, wherein mixing the sample and the at least one additive comprises mixing from about 1 nanogram to about 100 micrograms of the at least one additive.

6. The method of claim 1, wherein the substance of interest comprises a nitro-based sub stance.

7. The method of claim 6, wherein the nitro-based substance comprises at least one of ammonium nitrate (AN), ammonium nitrate fuel oil (ANFO), urea nitrate (UN), trinitrotoluene (TNT), ethylene glycol dinitrate (EGDN), nitroglycerin (NG), pentaerythritol tetranitrate (PETN), high melting explosive (HMX) and Research Department Explosive (RDX).

8. The method of claim 1, wherein the ionization source comprises at least one of an atmospheric pressure chemical ionization (APCI) source, an atmospheric pressure photoionization (APPI) source, an electrospray ionization (ESI) source and a direct analysis in real time (DART) source.

9. A substance detection system comprising:
   a reaction chamber housing defining a reaction chamber therein;
   a sample supply system coupled in flow communication with said reaction chamber, said sample supply system configured to channel at least a portion of a sample comprising at least one substance of interest to said reaction chamber;
   an additive system coupled in flow communication with said reaction chamber, said additive system configured to channel at least one additive to said reaction chamber, wherein the at least one additive includes at least one of an organic acid and an organic acid ester;
   an ionization source coupled in flow communication with said reaction chamber, said ionization source configured to produce an adduct from the at least a portion of a sample comprising at least one substance of interest and the at least one additive including at least one of an organic acid and an organic acid ester, wherein the adduct includes the at least one additive and a dissociated ion from the sample;

a spectrometric analysis device coupled in flow communication with said reaction chamber, said spectrometric analysis device configured to perform a spectrometric analysis of the adduct; and, a processor configured to identify at least one substance of interest using spectrometric data.

10. The substance detection system of claim 9, wherein the at least one additive comprises at least one of a carboxylic acid and a carboxylate.

11. The substance detection system of claim 10, wherein the carboxylic acid comprises at least one of benzoic acid, oxalic acid, and lactic acid.

12. The substance detection system of claim 10, wherein the carboxylate is a carboxylic acid ester.

13. The substance detection system of claim 9, wherein the additive system comprises from about 1 nanogram to about 100 micrograms of the at least one additive.

14. The substance detection system of claim 9, wherein the at least one substance of interest comprises a nitro-based substance.

15. The substance detection system of claim 14, wherein the nitro-based substance comprises at least one of ammonium nitrate (AN), ammonium nitrate fuel oil (ANFO), urea nitrate (UN), trinitrotoluene (TNT), ethylene glycol dinitrate (EGDN), nitroglycerin (NG), pentaerythritol tetranitrate (PETN), high melting explosive (HMX) and Research Department Explosive (RDX).

16. The substance detection system of claim 9, wherein the ionization source comprises at least one of an atmospheric pressure chemical ionization (APCI) source, an atmospheric pressure photoionization (APPI) source and an electrospray ionization (ESI) source.

17. A method for distinguishing different $NO_3^-$ ion structures, said method comprising:

collecting a sample comprising a nitro-based substance;

mixing the sample and at least one additive within a reaction chamber, wherein the at least one additive includes at least one of an organic acid and an organic acid ester;

using an ionization source to produce an adduct from the mixture of the sample and the at least one additive, wherein the adduct includes the at least one additive and a dissociated $NO_3^-$ ion from the sample;

performing a spectrometric analysis of the adduct; and, identifying an $NO_3^-$ ion structure using spectrometric data.

18. The method of claim 17, wherein the different $NO_3^-$ ion structures comprise at least one of nitrate $NO_3^-$ and atmospheric $NO_3^-$.

19. The method of claim 17, wherein the at least one additive comprises at least one of benzoic acid, oxalic acid, lactic acid and an oxalic acid ester.

20. The method of claim 17, wherein the nitro-based substance comprises at least one of ammonium nitrate (AN), ammonium nitrate fuel oil (ANFO), urea nitrate (UN), trinitrotoluene (TNT), ethylene glycol dinitrate (EGDN), nitroglycerin (NG), pentaerythritol tetranitrate (PETN), high melting explosive (HMX) and Research Department Explosive (RDX).

* * * * *